United States Patent [19]

Giano et al.

[11] Patent Number: 4,659,707
[45] Date of Patent: Apr. 21, 1987

[54] AMINOACYL DERIVATIVES OF 4,9-DIHYDRO-10H-PYRIDO[3,2-B]THIENO[3,2-E][1,4]DIAZEPINONE AND OF 4,9-DIHYDRO-10H-PYRIDO[3,2-B]THIENO[3,4-E][1,4]DIAZEPINONE, THEIR PREPARATION AND PHARMACEUTICAL COMPOSITIONS CONTAINING THEM

[75] Inventors: Roberto Giano; Ettore Parini; Salvatore Malandrino; Giancarlo Tonon, all of Milan, Italy

[73] Assignee: Dompe' Farmaceutici S.p.A., Milan, Italy

[21] Appl. No.: 891,696

[22] Filed: Jul. 29, 1986

[30] Foreign Application Priority Data

Aug. 16, 1985 [DE] Fed. Rep. of Germany ....... 3529372

[51] Int. Cl.$^4$ ..................... A61K 495/14; C07D 31/55
[52] U.S. Cl. .................... 514/215; 540/495; 546/284
[58] Field of Search ......................... 540/495; 514/215

[56] References Cited

U.S. PATENT DOCUMENTS 4,424,225  1/1984  Schmidt et al. .................... 540/495

Primary Examiner—Robert T. Bond
Attorney, Agent, or Firm—Walter H. Schneider

[57] ABSTRACT

Compounds of the formula I

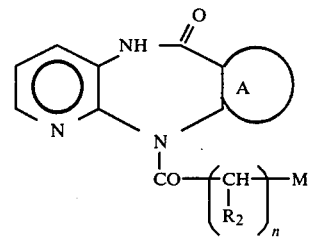

wherein the A ring represents

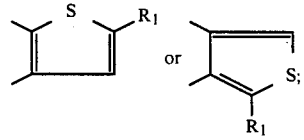

$R_1$ and $R_2$ are H or $CH_3$; M is a cyclic amino group, are endowed with antiulcer, antisecretory, antimuscarinic and spasmolytic activity.

9 Claims, No Drawings

AMINOACYL DERIVATIVES OF 4,9-DIHYDRO-10H-PYRIDO[3,2-B]THIENO[3,2-E][1,4]DIAZEPINONE AND OF 4,9-DIHYDRO-10H-PYRIDO[3,2-B]THIENO[3,4-E][1,4]DIAZEPINONE, THEIR PREPARATION AND PHARMACEUTICAL COMPOSITIONS CONTAINING THEM

The present invention relates to compounds of the general formula (I)

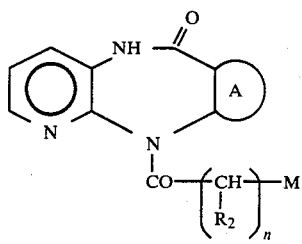

wherein
A is

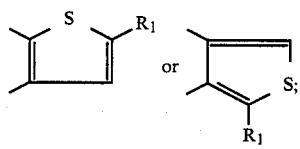

$R_1$ is hydrogen or methyl;
n is 0, 1 or 2;
$R_2$ is hydrogen or methyl when n is 1 and is hydrogen when n is 2;
when n is different than zero, M is a 5- or 6-membered cyclic amino group, optionally containing another heteroatom such as oxygen, sulfur or nitrogen;
when n is zero, M is one of the following groups:

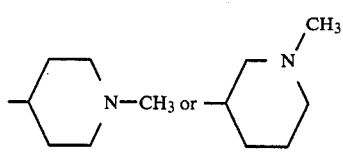

their salts with pharmaceutically acceptable acids and possible enantiomeric forms thereof.

The cyclic amino group, optionally containing another heteroatom, comprises, according to the invention, the following groups: 1-pyrrolidinyl, 1-thiazolidinyl, 1-piperidinyl, 1-morpholinyl, 1-piperazinyl, 1-(4-methyl)piperazinyl.

1-Piperidinyl and 1-(4-methyl)-piperazinyl groups are particularly preferred.

In U.S. Pat. No. 3,953,430 compounds of formula II

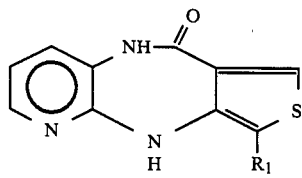

are disclosed as intermediates for the preparation of compounds having activity on the central nervous system.

On the contrary, the compounds I, object of the present invention, are endowed with interesting anti-ulcer, anti-secretory, anti-muscarinic and spasmolytic activity. A further object of the invention is therefore provided by pharmaceutical compositions containing the compound I as the active principle.

Another object of the invention is also provided by a process of the preparation of compounds I comprising the reaction of a tricyclic compound having formula III or IV

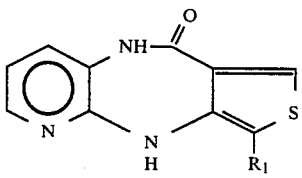

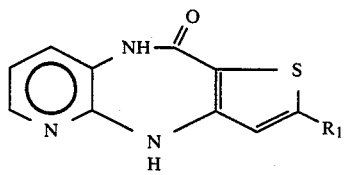

wherein $R_1$ has the above defined meaning, with haloacid chlorides of formula V

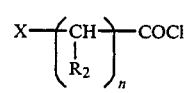

wherein $R_2$ and n have the above defined meanings and X is Cl, Br or I, preferably Cl, or with activated derivatives of N-methyl-nipecotic or -isonipecotic acid, such as chlorides or anhydrides.

The compounds obtained from the reaction with the chlorides of formula V are then reacted with the previously cited cyclic amines, such as pyrrolidine, thiazolidine, piperidine, piperazine, 4-methyl-piperazine and so on, to give the compounds I. The reaction between the tricyclic compounds III or IV and the acyl chlorides V or N-methylnipecotic and -isonipecotic acid chloride is preferably carried out in inert solvents, such as dimethylformamide, pyridine, dioxane, tetrahydrofuran, in the presence of a base such as triethylamine, pyridine or alkali carbonates or bicarbonates, at the solvent's reflux temperature, for times ranging from 2 to 24 hours, or from 0.5 to 4 hours in the instance of N-methyl-nipecotic and N-methyl-isonipecotic acid chlorides.

Also the reaction between the haloacyl derivatives obtained from the reaction of V with III or IV is carried out in inert solvents such as dioxane, tetrahydrofurane, benzene, toluene, dimethylformamide, alcohols, preferably in the presence of a base which can be an excess of the reagent amine itself, or triethylamine, alkali hydroxides and carbonates. The reaction temperature ranges from the room temperature and the solvent's reflux temperature, for times ranging from 1 to 24 hours.

The compounds III are known from U.S. Pat. No. 3,953,430 whereas the compounds IV, per se new and providing therefore another object of the invention, being useful as intermediates, may be prepared by reductive cyclization of the nitroester of formula VI

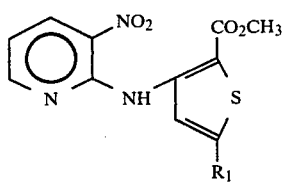

wherein $R_1$ has the above defined meanings, preferably by means of $SnCl_2$ in concentrated aqueous HCl.

In its turn, the compound VI may be prepared by reaction of 2-chloro-3-nitropyridine VII and the methylester of 3-aminothiophen-2-carboxylic acid VIII, according to the following scheme:

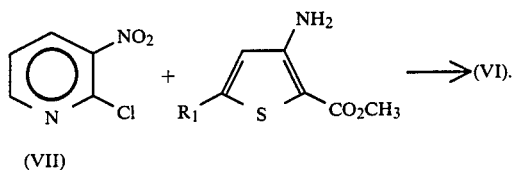

The reaction is preferably carried out in an inert solvent such as chlorobenzene, trichlorobenzene, isoamyl alcohol, or without solvent, at temperatures ranging from 100° to 200° C., optionally in the presence of bases.

The reaction times are ranging from 2 to 12 hours.

The following non-limitative examples further illustrate the invention.

EXAMPLE 1

(a) 3-(3-Nitropyridin-2-yl)-aminothiophen-2-carboxylic acid, methylester

2-Chloro-3-nitroaniline (35 g) and methyl-3-aminothiophene-2-carboxylate (34.5 g) are heated to 150° C. for 8 hours. The reaction mixture, after cooling, is dissolved in chloroform. The insoluble impurities are filtered off and the filtrate, decolorized on charcoal, is evaporated.

The residue, triturated with ethanol, yields 17.5 g (28.3%) of the title product, melting at 180°–183° C.

| Microanalysis | C | H | N | S |
|---|---|---|---|---|
| Calc. % | 47.31 | 3.25 | 15.05 | 11.48 |
| Found % | 47.25 | 3.22 | 14.98 | 11.36. |

(b) 5-Methyl-3-(3-nitropyridin-2-yl)-aminothiophene-2-carboxylic acid, methylester Following the same process described in the Example 1, using 5-methyl-3-aminothiophene-2-carboxylic acid methyl ester, the title product is obtained.

Yield 44.8%; m.p. 171°–174° C.

| Microanalysis | C | H | N | S |
|---|---|---|---|---|
| Calc. % | 49.14 | 3.78 | 14.33 | 10.93 |
| Found % | 48.97 | 3.84 | 14.30 | 11.01. |

(c) 4,9-Dihydro-10H-pyrido[3,2-b]thieno[3,2-e][1,4]-diazepin-10-one 3-(3-Nitropyridin-2-yl)aminothiophene-2-carboxylic acid methylester (14.6 g) is added to a suspension of dihydrate tin chloride (64 g) in conc. HCl (210 ml) and ethanol (235 ml). The reaction mixture is refluxed for 2 hours obtaining the gradual dissolution of the reagents and subsequent precipitation of a solid. After cooling at the room temperature, the solid is filtered and triturated with a saturated solution of $NaHCO_3$, filtered, washed with $H_2O$ and dried to give 6.4 g (56%) of the title product, melting at 273°–279° C.

| Microanalysis | C | H | N | S |
|---|---|---|---|---|
| Calc. % | 55.29 | 3.25 | 19.34 | 14.76 |
| Found % | 55.10 | 3.33 | 19.20 | 14.58. |

EXAMPLE 2

2-Methyl-4,9-dihydro-10H-pyrido[3,2-b]thieno[3,2-e][1,4]-diazepin-10-one

According to the same procedure described in the Example 1, using the methylester of 5-methyl-3-(3-nitropyridine-2-yl)-amino-thiophen-2-carboxylic acid, the title product is obtained.

Yield 68%; m.p. 254° C. (decomposition).

| Microanalysis | C | H | N | S |
|---|---|---|---|---|
| Calc. % | 57.13 | 3.92 | 18.17 | 13.86 |
| Found % | 56.95 | 4.01 | 18.10 | 13.85. |

EXAMPLE 3

(a) 4-Chloroacetyl-4,9-dihydro-10H-pyrido[3,2-b]thieno[3,2-e][1,4]-diazepin-10-one Chloroacetyl chloride (1.9 ml) is added in 20 minutes, contemporaneously with triethylamine (3.4 ml), to a suspension of 4,9-dihydro-10H-pyrido[3,2-b]thieno[3,2-e][1,4]-diazepin-10-one (4.4 g) in dioxane (200 ml), heated to reflux.

The reaction mixture is heated to reflux for 6 hours, then hot-filtered. The clear solution is evaporated. The residue, triturated with methylene chloride, yields 1.8 g of the title product (30.7%), melting at 266°–267° C. (dec.).

| Microanalysis | C | H | Cl | N | S |
|---|---|---|---|---|---|
| Calc. % | 49.07 | 2.74 | 12.07 | 14.30 | 10.91 |
| Found % | 48.95 | 2.69 | 12.21 | 14.31 | 11.01. |

(b) 4-[(4-Methylpiperazin-1-yl)acetyl]-4,9-dihydro-10H-pyrido[3,2-b]thieno[3,2-e][1,4]-diazepin-10-one hydrochloride A suspension of the compound obtained in (a) and N-methylpiperazine (1 ml) in dioxane (30 ml) is refluxed for 2 hours. After cooling, the solid is filtered and recrystallized from an acetonitrile-ethanol mixture to give 0.5 g of the title product (37.7%) melting at 242°–246° C. (dec.).

| Microanalysis | C | H | N | S |
|---|---|---|---|---|
| Calc. % | 51.84 | 5.12 | 17.78 | 8.14 |
| Found % | 52.01 | 5.15 | 17.81 | 8.10. |

EXAMPLE 4

4-(2-Chloropropionyl)-4,9-dihydro-10H-pyrido[3,2-b]thieno[3,2-e][1,4]-diazepin-10-one According to the method or the Example 3(a), using 2-chloropropionyl chloride, the title product is obtained.

Yield 20%. M.p. 198°–201° C. (dec.)($CH_2Cl_2$).

| Microanalysis | C | H | Cl | N | S |
|---|---|---|---|---|---|
| Calc. % | 50.74 | 3.27 | 11.52 | 13.65 | 10.42 |
| Found % | 50.84 | 3.33 | 11.62 | 13.48 | 10.37. |

EXAMPLE 5

4-(3-Chloropropionyl)-4,9-dihydro-10H-pyrido[3,2-b]thieno[3,2-e][1,4]-diazepin-10-one According to the method described in the Example 3(a), using 3-chloropropionyl chloride, the title product is obtained.

Yield 14.6%.

| Microanalysis | C | H | Cl | N | S |
|---|---|---|---|---|---|
| Calc. % | 50.74 | 3.27 | 11.52 | 13.65 | 10.42 |
| Found % | 50.80 | 3.28 | 11.41 | 13.51 | 10.48. |

EXAMPLE 6

(a)

2-Methyl-4-chloroacetyl-4,9-dihydro-10H-pyrido[3,2-b]thieno[3,2-e][1,4]-diazepin-10-one According to the method described in Example 3(a), using as starting material 2-methyl-4,9-dihydro-10H-pyrido[3,2-b]thieno[3,2-e][1,4]-diazepin-10-one, the title compound has been obtained. Yield: 26.8%, m.p. 269°–272° C. (dec.)(dioxane).

| Microanalysis | C | H | Cl | N | S |
|---|---|---|---|---|---|
| Calc. % | 50.74 | 3.27 | 11.52 | 13.65 | 10.42 |
| Found % | 50.62 | 3.28 | 11.58 | 13.54 | 10.40. |

(b)

2-Methyl-4[(4-methyl-piperazin-1-yl)acetyl]-4,9-dihydro-10H-pyrido[3,2-b]thieno[3,2-e][1,4]-diazepin-10-one A suspension of the product obtained in (a) (5 g) and N-methylpiperazine (4.3 ml) in dioxane-ethanol 9:1 (50 ml) is heated to reflux for 2 hours. After cooling and filtration of the insoluble impurities, the clear filtrate is evaporated and the residue dissolved in chloroform (100 ml). The solution is washed with a diluted ammonium hydroxyde solution (20 ml), dried, decolorized and evaporated. The residue, crystallized from methanol, yields 2.2 g of the title product, melting at 273°–275° C. (dec.).

| Microanalysis | C | H | N | S |
|---|---|---|---|---|
| Calc. % | 58.20 | 5.70 | 18.85 | 8.63 |
| Found % | 58.18 | 5.68 | 18.91 | 8.66. |

EXAMPLE 7

4-(N-Methyl-isonipecotinoyl)-4,9-dihydro-10H-pyrido[3,2-b]thieno[3,2-e][1,4]-diazepin-10-one A suspension of N-methyl-isonipecotic acid chloride (15 g) in dioxane (50 ml), in 4 portions, is added to a suspension of 4,9-dihydro-10H-pyrido[3,2-b]thieno[3,2-e][1,4]-diazepin-10-one (10 g) in dioxane (200 ml) and pyridine (40 ml), heated to reflux. The mixture is refluxed for 3 hours and then evaporated. The residue is dissolved in water and the pH of the solution is adjusted to 10 with conc. ammonia. The solution is then repeatedly extracted with chloroform and the collected organic extracts are evaporated. The residue, crystallized from acetonitrile, yields 5.9 g of the title product, melting at 280°–282° C.

| Microanalysis | C | H | N | S |
|---|---|---|---|---|
| Calc. % | 59.63 | 5.30 | 16.36 | 9.36 |
| Found % | 59.58 | 5.33 | 16.31 | 9.40. |

EXAMPLES 8–12

According to the procedures described in the previous examples, the compounds reported in the following table, having formula:

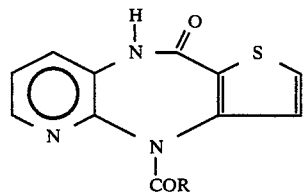

have been obtained.

TABLE 1

| No. | R | Yield % | M.p. °C. | Calc. % C | H | N | S | Found % C | H | N | S |
|---|---|---|---|---|---|---|---|---|---|---|---|
| 8 | 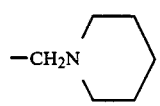 | 33 | 214–216 | 59.63 | 5.30 | 16.36 | 9.36 | 59.61 | 5.33 | 16.40 | 9.41 |

TABLE 1-continued

| No. | R | Yield % | M.p. °C. | Calc. % C | H | N | S | Found % C | H | N | S |
|---|---|---|---|---|---|---|---|---|---|---|---|
| 9 | —CHN⟨NCH₃⟩·HCl<br>  \|<br>  CH₃ | 44 | 253 (dec.) | 53.00 | 5.44 | 17.17 | 7.86 | 52.94 | 5.48 | 17.10 | 7.90 |
| 10 | —CHN⟨⟩<br>  \|<br>  CH₃ | 34 | 226–229 (dec.) | 60.65 | 5.65 | 15.72 | 8.99 | 60.61 | 5.70 | 15.71 | 9.01 |
| 11 | —CH₂CH₂N⟨NCH₃⟩ | 59 | 226–229 | 58.20 | 5.70 | 18.85 | 8.63 | 58.12 | 5.74 | 18.84 | 8.58 |
| 12 | —CH₂CH₂N⟨⟩ | 54 | 220–223 | 60.65 | 5.65 | 15.72 | 8.99 | 60.63 | 5.65 | 15.79 | 9.03 |

EXAMPLE 13

(a)

4-Chloroacetyl-4,9-dihydro-10H-pyrido[3,2-b]thieno[3,4-e][1,4]-diazepin-10-one

Chloroacetyl chloride (3.4 ml) is added in 20 minutes, contemporaneously with triethylamine (5.8 ml), to a suspension of 4,9-dihydro-10H-pyrido[3,2-b]thieno[3,4-e][1,4]-diazepin-10-one (6.5 g) in dioxane (200 ml), kept under reflux. The reaction mixture is refluxed for 1 hour, then it is hot filtered. The clear solution is evaporated and the residue, triturated with ethyl acetate, yields 6.4 g of the title product, melting at 264°–266° C.

| Microanalysis | C | H | Cl | N | S |
|---|---|---|---|---|---|
| Calc. % | 49.07 | 2.74 | 12.07 | 14.30 | 10.91 |
| Found % | 48.98 | 2.76 | 12.15 | 14.32 | 10.94. |

(b)

4-[(4-Methylpiperazin-1-yl)acetyl]-4,9-dihydro-10H-pyrido[3,2-b]thieno[3,4-e][1,4]-diazepin-10-one A suspension of the product obtained in (a) (2.4 g) and N-methyl-piperazine (1.8 ml) in dioxane (50 ml) is refluxed for 1 hour. After evaporation, the residue is dissolved in chloroform and washed with water. The organic phase, after drying and decoloration, is evaporated to dryness. The residue, crystallized from acetonitrile, yields 1.1 g of the title compound, melting at 228°–230° C.

| Microanalysis | C | H | N | S |
|---|---|---|---|---|
| Calc. % | 51.84 | 5.12 | 17.78 | 8.14 |
| Found % | 51.91 | 5.09 | 17.82 | 8.08. |

EXAMPLE 14

(a)

3-Methyl-4-chloroacetyl-4,9-dihydro-10H-pyrido[3,2-b]thieno[3,4-e][1,4]-diazepin-10-one According to the method described in Example 13a, using as the starting material 3-methyl-4,9-dihydro-10H-pyrido[3,2-b]thieno[3,4-e][1,4]-diazepin-10-one, the title product has been prepared.

Yield 60.1%, m.p. 196°–198° C. (ethyl acetate).

| Microanalysis | C | H | Cl | N | S |
|---|---|---|---|---|---|
| Calc. % | 50.74 | 3.27 | 11.52 | 13.65 | 10.42 |
| Found % | 50.89 | 3.35 | 11.40 | 13.51 | 10.47. |

(b)

4-[(4-Methylpiperazin-1-yl)acetyl]-3-methyl-4,9-dihydro-10H-pyrido[3,2-b]thieno[3,4-e][1,4]-diazepin-10-one From the product obtained in (a), according to the method described in the Example 12, the title product has been obtained (yield 35%), m.p. 238°–240° C. (acetonitrile).

| Microanalysis | C | H | N | S |
|---|---|---|---|---|
| Calc. % | 58.20 | 5.70 | 18.85 | 8.63 |
| Found % | 58.31 | 5.72 | 18.71 | 8.60. |

EXAMPLE 15

4-(N-Methyl-isonipecotinoyl)-4,9-dihydro-10H-pyrido[3,2-b]thieno[3,4-e][1,4]-diazepin-10-one A suspension of N-methyl-isonipecotic acid chloride (2.9 g) in dioxane (10 ml) is added in 4 portions to a suspension of 4,9-dihydro-10H-pyrido[3,2-b]thieno[3,4-e][1,4]-diazepin-10-one (1.9 g) in dioxane (50 ml) and pyridine (10 ml) heated to reflux. The reflux is continued for 1 hour and the mixture is then evaporated to dryness. The residue is dissolved in water and alkalinized to pH 11 with conc. ammonia. The solution is repeatedly extracted with chloroform and the collected organic extracts are concentrated to small volume. 0.5 Grams of the title product are obtained after standing, m.p. 274°–278° C.

| Microanalysis | C | H | N | S |
|---|---|---|---|---|
| Calc. % | 59.63 | 5.30 | 16.36 | 9.36 |
| Found % | 59.60 | 5.38 | 16.28 | 9.31. |

EXAMPLE 16

4-(N-Methyl-isonipecotinoyl)-3-methyl-4,9-dihydro-10H-pyrido[3,4-b]thieno[3,4-e][1,4]-diazepin-10-one Starting from 3-methyl-4,9-dihydro-10H-pyrido[3,2-b]thieno[3,4-e][1,4]-diazepin-10-one, according to the method described in the previous Example, the title product has been obtained.

Yield 54%, m.p. 208°–210° C.

| Microanalysis | C | H | N | S |
|---|---|---|---|---|
| Calc. % | 60.65 | 5.65 | 15.72 | 8.99 |
| Found % | 60.42 | 5.61 | 15.78 | 9.03. |

EXAMPLE 17

4-(N-Methyl-nipecotinoyl)-4,9-dihydro-10H-pyrido[3,2-b]thieno[3,4-e][1,4]-diazepin-10-one To the boiling suspension of 4,9-dihydro-10H-pyrido[3,2-b]thieno[3,4-e][1,4]-diazepin-10-one (9 g) in dioxane (120 ml) and pyridine (30 ml), a suspensione of N-methyl-nipecotinoyl chloride hydrochloride (9.5 g) in dioxane (30 ml), in four portions, is added. The reflux is continued for 1 hour and the mixture is then evaporated to dryness. The residue is dissolved in water and brought to pH 11 with concentrated ammonia; the solution is repeatedly extracted with CHCl$_3$, the collected organic extracts are evaporated to dryness and the residue is crystallized from diethyl ether. Five grams of the title product, m.p. 151°–153° C. (dec.) are obtained.

| Microanalysis | C | H | N | S |
|---|---|---|---|---|
| Calc. % | 59.63 | 5.30 | 16.36 | 9.36 |
| Found % | 59.45 | 5.30 | 16.41 | 9.28. |

The compounds of the Examples 3, 13 and 14 have been subjected to pharmacological testing, using the following methods:

1. Gastric acid secretion in the pylorus ligated rat

The method of Shay H., Kamarov S. A., Fels, S. S., Meranee D., Gruenstein M., Siplet H., Gastroenterology, 5, 43 (1945) was used, slightly modified according to the following:

Male Sprague-Dawley rats weighing 150±5 g fasting since 48 hours were used. Pylorus ligation was performed for 4 hours. The products under exam were administered by the oral route immediately after the ligation.

2. Stress ulcer (restraint+immersion) in the rat

The method described by Takagi, K., Okabes, S., Jap. J. Pharmacol., 18, 9 (1968) has been used. The animals fasted for 48 hours were immobilized in a stress cage (drilled cylindrical tube 14.5×3.5 cm) and immersed in H$_2$O (at a temperature of about 20° C.) up to the xiphoid process. After 6 hours immersion the animals were sacrificed in excess ether, the stomach was drawn and opened along the great curvature.

The ulcers were evaluated according to a score ranging from 0 to 5 assigning:

0.5 for each small ulcera (<3 mm) or in the presence of erosions or haemorrages 1 for each great ulcer (>3 mm).

The oral treatment with the reference drug pirenzepine at the doses of 12.5—25—50 mg/kg has been carried out 1 hour before the stress.

3. Charbacole salivation in the rat

The method cited by R. Turner: "Parasympatholytic Agents" in R. Turner "Screening Methods in Pharmacology" pag. 137. Academic Press. New York & London 1965, with slight changes, was used. Male Sprague-Dawley rats, average weight 150±5 g, fasted for 24 hours, were used.

The salivation was induced by the intraperitoneal administration of 1 mg/kg of charbacole.

The products under exam were administered orally one hour before the chollinergic stimulus.

4. Oxotremorine tremors in the mouse

The method described by Brimblecambe, R. W., Green, D. M., Int. J. Neuropharmacol., 7, 15, 1968 has been used. The tremors in mice were induced by intraperitoneal administration of 2 mg/kg oxotremorine.

In the treated animals, the tremors appear evident within 10 minutes from the oxotremorine injection.

The compounds under exam have been administered by oral route 60 minutes before the stimulus.

The results are expressed as percentages of protected animals.

5. Acute toxicity

The acute toxicity was determined by administering by oral route the substances under exam to Swiss mice; average weight 20±2 g. The observation period was 14 days. 10 Animals were used for each tested dose.

The results of the pharmacological and toxicological tests are reported in the following Table 2.

TABLE 2

| | PHARMACOLOGICAL ACTIVITY | | | | |
|---|---|---|---|---|---|
| Compound Ex. No. | Antisecretory activity ED$_{50}$ mg/kg (confidence limits p = 0.95) | Antiulcer activity (stress ulcer) ED$_{50}$ mg/kg (confidence limits p = 0.95) | Carbachole salivation ED$_{50}$ mg/kg (confidence limits p = 0.95) | Tremors by oxotremorine ED$_{50}$ mg/kg (confidence limits p = 0.95) | Acute toxicity LD$_{50}$ mg/kg |
| 3 | 27.58 (20.16–35.90) | 55.90 (41.23–75.79) | >200 | >1000 | >2000 |
| 13 | 12.40 (7.21–19.16) | 28.75 (22.74–36.36) | >200 | >1000 | >1000 |
| 14 | 3.12 | 4.43 | 3.36 | >10000 | >500 |

TABLE 2-continued

PHARMACOLOGICAL ACTIVITY

| Compound Ex. No. | Antisecretory activity ED$_{50}$ mg/kg (confidence limits p = 0.95) | Antiulcer activity (stress ulcer) ED$_{50}$ mg/kg (confidence limits p = 0.95) | Carbachole salivation ED$_{50}$ mg/kg (confidence limits p = 0.95) | Tremors by oxotremorine ED$_{50}$ mg/kg (confidence limits p = 0.95) | Acute toxicity LD$_{50}$ mg/kg |
|---|---|---|---|---|---|
| | (2.16–4.89) | (2.40–8.18) | | | |

From the above data, it is evident the utility of compounds I as antiulcer, antisecretory, antimuscarinic and spasmolytic agents in human therapy.

For the use as a drug, the compounds of the invention or non-toxic salts thereof can be administered by oral or parenteral route.

Suitable dosage forms for the oral administration comprise capsules, tablets, granules, syrups. For parenteral administration suitable dosage forms are sterile injectable solutions. These dosage forms are prepared using conventional methods and excipients, formulating the active ingredients with suitable carriers, excipients, binding agents, preservative agents, stabilizers, flavouring agents etc. The compositions of the invention can optionally comprise other active principles having complementar or anyhow useful activity.

We claim:

1. A compound of formula I

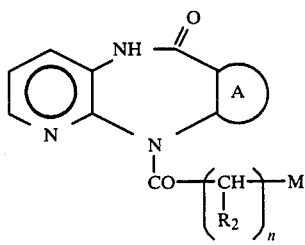

wherein
A is

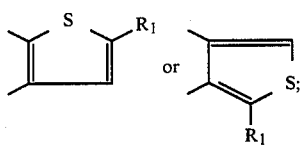

$R_1$ is hydrogen or methyl;
n is 0, 1 or 2;
$R_2$ is hydrogen or methyl when n is 1 and is hydrogen when n is 2;
when n is different than zero, M is a 5- or 6-membered cyclic amino group, optionally containing another heteroatom such as oxygen, sulfur or nitrogen;
when n is zero, M is one of the following groups:

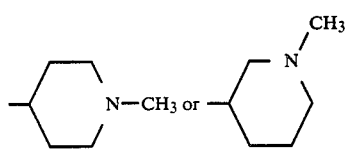

their salts with pharmaceutically acceptable acids and possible enantiomeric forms thereof.

2. A compound according to claim 1 wherein A is

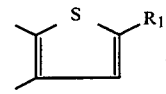

3. A compound according to claim 1 wherein A is

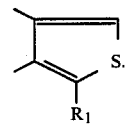

4. A compound according to claim 1, wherein the cyclic amine group is selected in the group consisting of 1-pyrrolidinyl, 1-thiazolidinyl, 1-piperidinyl, 1-morpholinyl, 1-piperazinyl, 1-(4-methyl)piperazinyl.

5. A compound according to claim 1 wherein the cyclic amine group is 1-piperidinyl or (4-methyl)-1-piperazinyl.

6. A process for the preparation of a compound according to formula I characterized in that a compound of formula III or IV

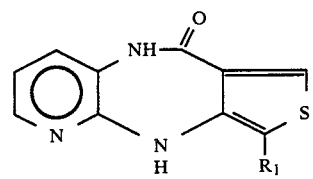

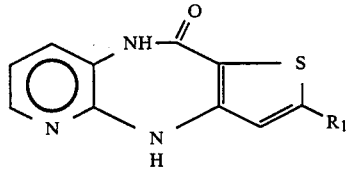

is reacted with an acyl chloride of formula V

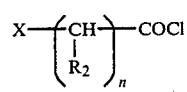

wherein $R_2$ and n are as above defined and X is Cl, Br or I or with an activated derivative of nipecotic or isonipecotic acids and that the product obtained from the reaction with an acyl chloride of formula V is then reacted with amine selected in the group of pyrrolidine, thiazolidine, morpholine, piperidine, piperazine, 4-methyl-piperazine.

7. A process according to claim 6 characterized in that the reaction is carried out in inert solvent and in the presence of base as acidity acceptor.

8. A compound of formula IV

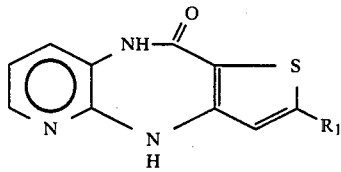

(IV)

wherein $R_1$ is methyl or hydrogen.

9. A pharmaceutical composition having antiulceric, antisecretoric, antimuscarinic and spasmolytic activity comprising as the principal active ingredient an effective amount of at least one compound according to formula I together with a pharmaceutically acceptable carrier.

* * * * *

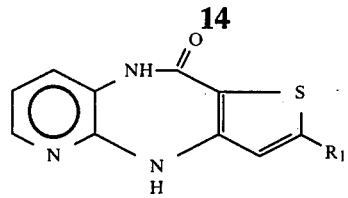

(IV)

wherein $R_1$ is methyl or hydrogen.

9. A pharmaceutical composition having antiulceric, antisecretoric, antimuscarinic and spasmolytic activity comprising as the principal active ingredient an effective amount of at least one compound according to formula I together with a pharmaceutically acceptable carrier.

* * * * *